United States Patent
Lorain et al.

(10) Patent No.: US 10,471,089 B2
(45) Date of Patent: Nov. 12, 2019

(54) COMBINED THERAPY FOR DUCHENNE MUSCULAR DYSTROPHY

(71) Applicants: ASSOCIATION INSTITUT DE MYOLOGIE, Paris (FR); INSERM (INSTITUT NATIONAL DE LA SANTE ET DE LA RECHERCHE MEDICALE), Paris (FR); UNIVERSITE PIERRE ET MARIE CURIE (PARIS 6), Paris (FR); CENTRE NATIONAL DE LA RECHERCHE SCIENTIFIQUE, Paris (FR)

(72) Inventors: Stephanie Lorain, Vincennes (FR); Thomas Voit, London (GB); Matthew Wood, Oxford (GB); Graham McClorey, Oxford (GB)

(73) Assignees: ASSOCIATION INSTITUT DE MYOLOGIE, Paris (FR); SORBONNE UNIVERSITE, Paris (FR); CENTRE NATIONAL DE LA RECHERCHE SCIENTIFIQUE, Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 0 days.

(21) Appl. No.: 15/735,094

(22) PCT Filed: Jun. 10, 2016

(86) PCT No.: PCT/EP2016/063404
§ 371 (c)(1),
(2) Date: Dec. 8, 2017

(87) PCT Pub. No.: WO2016/198676
PCT Pub. Date: Dec. 15, 2016

(65) Prior Publication Data
US 2018/0169130 A1 Jun. 21, 2018

(30) Foreign Application Priority Data
Jun. 10, 2015 (EP) .................................... 15305890

(51) Int. Cl.
| | |
|---|---|
| *C07H 21/04* | (2006.01) |
| *A61K 31/712* | (2006.01) |
| *C12N 15/11* | (2006.01) |
| *C12N 15/113* | (2010.01) |
| *A61P 43/00* | (2006.01) |
| *C07K 14/435* | (2006.01) |
| *C12N 15/86* | (2006.01) |

(52) U.S. Cl.
CPC ............ *A61K 31/712* (2013.01); *A61P 43/00* (2018.01); *C07K 14/435* (2013.01); *C12N 15/111* (2013.01); *C12N 15/113* (2013.01); *C12N 15/86* (2013.01); *C12N 2310/11* (2013.01); *C12N 2310/3233* (2013.01); *C12N 2310/3513* (2013.01); *C12N 2320/31* (2013.01); *C12N 2320/32* (2013.01)

(58) Field of Classification Search
CPC .................................................... C12N 15/111
See application file for complete search history.

(56) References Cited

PUBLICATIONS

Echevarría, Lucía, Philippine Aupy, and Aurélie Goyenvalle. "Exon-skipping advances for Duchenne muscular dystrophy." Human molecular genetics (2018).*
Wu, Bo, et al. ("Targeted skipping of human dystrophin exons in transgenic mouse model systemically for antisense drug development." PloS one 6.5 (2011): e19906).*
Chamberlain et al. ("Progress toward gene therapy for Duchenne muscular dystrophy." Molecular Therapy 25.5 (2017): 1125-1131).*
Le Hir et al: "AAV Genome Loss From Dystrophic Mouse Muscles During AAV-U7 snRNA-mediated Exon-skipping Therapy", Molecular Therapy, vol. 21, No. 8, Aug. 1, 2013 (Aug. 1, 2013), pp. 1551-1558.
Hoogaars et al: "Combined Effect of AAV-U7-Induced Dystrophin Exon Skipping and Soluble Activin Type IIB Receptor in mdx Mice", Human Gene Therapy, vol. 23, No. 12, Dec. 1, 2012 (Dec. 1, 2012), pp. 1269-1279.
Le Guiner et al: "Forelimb Treatment in a Large Cohort of Dystrophic Dogs Supports Delivery of a Recombinant AAV for Exon Skipping in Duchenne Patients", Molecular Therapy, vol. 22, No. 11, Aug. 4, 2014 (Aug. 4, 2014), pp. 1923-1935.
Dupont et al: "Short-lived recombinant adeno-associated virus transgene expression in dystrophic muscle is associated with oxidative damage to transgene mRNA", Molecular Therapy—Methods & Clinical Development, vol. 2, Apr. 8, 2015 (Apr. 8, 2015), p. 15010.
Betts et al: "Prevention of exercised induced cardiomyopathy following Pip-PMO treatment in dystrophic mdx mice", Scientific Reports, vol. 5, Mar. 11, 2015 (Mar. 11, 2015), p. 8986.
European Patent Office, International Search Report in PCT/EP2016/063404, dated Oct. 4, 2016.

* cited by examiner

*Primary Examiner* — Kimberly Chong
(74) *Attorney, Agent, or Firm* — Arrigo, Lee, Guttman & Mouta-Bellum LLP

(57) ABSTRACT

The present invention relates to the combined use of antisense oligonucleotides and viral vectors for the treatment of Duchenne muscular dystrophy.

Figure 1:
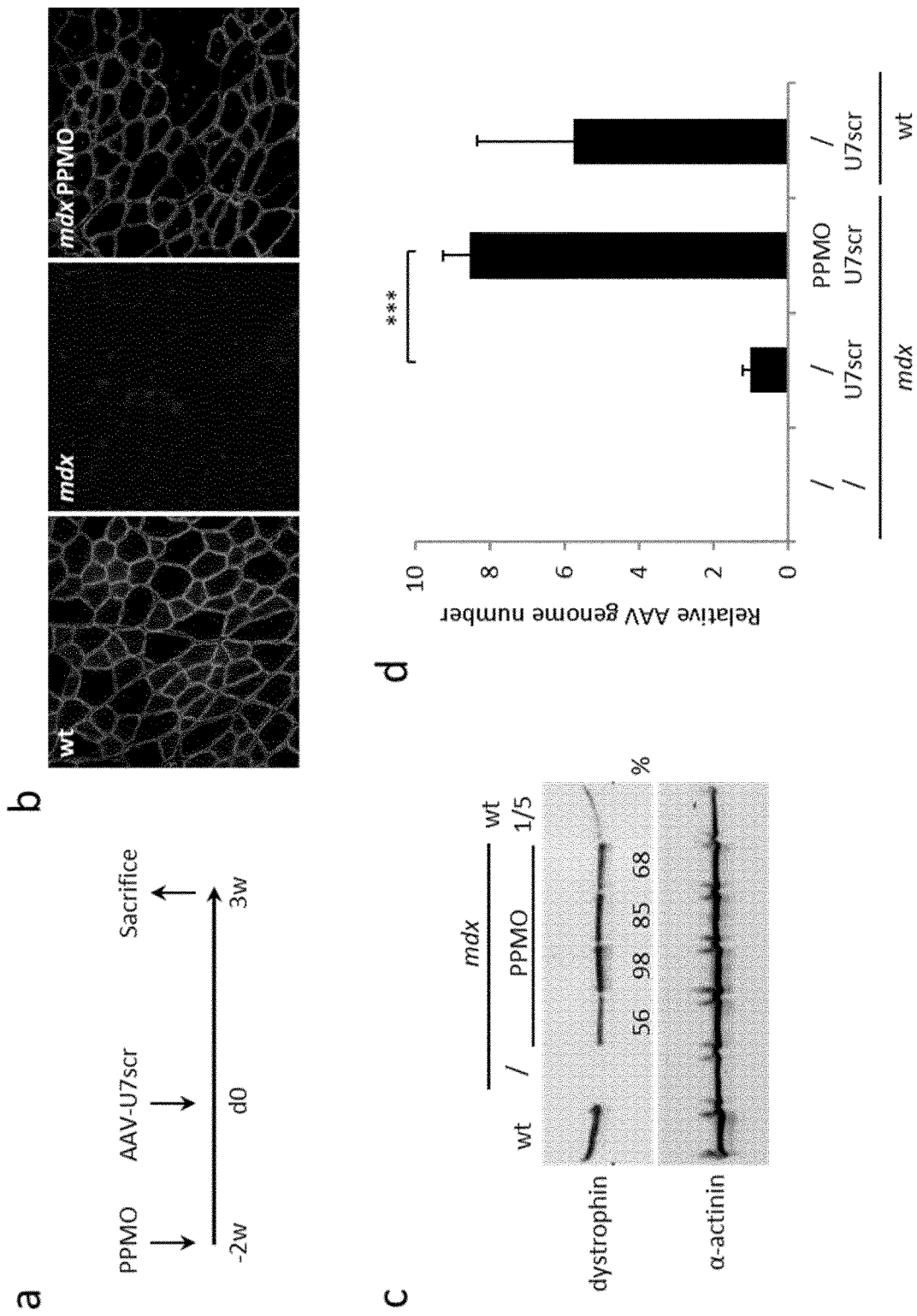

13 Claims, 3 Drawing Sheets
Specification includes a Sequence Listing.

SEQUENCE LISTING

<160> NUMBER OF SEQ ID NOS: 7

<210> SEQ ID NO 1
<211> LENGTH: 25
<212> TYPE: DNA
<213> ORGANISM: artificial
<220> FEATURE:
<223> OTHER INFORMATION: antisense oligonucleotide

<400> SEQUENCE: 1
ggccaaacct cggcttacct gaaat                     25

<210> SEQ ID NO 2
<211> LENGTH: 44
<212> TYPE: DNA
<213> ORGANISM: artificial
<220> FEATURE:
<223> OTHER INFORMATION: U7-modified antisense oligonucleotide

<400> SEQUENCE: 2
ggccaaacct cggcttacct aaatagaagt tcatttacac taac     44

<210> SEQ ID NO 3
<211> LENGTH: 22
<212> TYPE: DNA
<213> ORGANISM: artificial
<220> FEATURE:
<223> OTHER INFORMATION: primer

<400> SEQUENCE: 3
ctccatcact aggggttcct tg                        22

<210> SEQ ID NO 4
<211> LENGTH: 18
<212> TYPE: DNA
<213> ORGANISM: artificial
<220> FEATURE:
<223> OTHER INFORMATION: primer

<400> SEQUENCE: 4
gtagataagt agcatggc                             18

<210> SEQ ID NO 5
<211> LENGTH: 17
<212> TYPE: DNA
<213> ORGANISM: artificial
<220> FEATURE:
<223> OTHER INFORMATION: probe

<400> SEQUENCE: 5
tagttaatga ttaaccc                              17

<210> SEQ ID NO 6
<211> LENGTH: 3765
<212> TYPE: DNA
<213> ORGANISM: artificial
<220> FEATURE:
<223> OTHER INFORMATION: optimized delta-AB/R3-R18/delta CT

<400> SEQUENCE: 6
gccaccatgc tgtggtggga ggaagtggag gactgctacg agagagagga cgtgcagaag     60
aaaaccttca ccaagtgggt gaacgcccag ttcagcaagc acctggaggc ccctgaggac    120

```
aagagcttcg gcagcagcct gatggagagc gaagtgaacc tggacagata ccagaccgcc    180
ctggaggaag tgctgagctg gctgctgagc gccgaggaca ccctgcaggc ccagggcgag    240
atcagcaacg acgtggaagt ggtgaaggac cagttccaca cccacgaggg ctacatgatg    300
gatctgaccg cccaccaggg cagagtgggc aatatcctgc agctgggcag caagctgatc    360
ggcaccggca agctgagcga ggacgaggag accgaagtgc aggagcagat gaacctgctg    420
aacagcagat gggagtgcct gagagtggcc agcatggaga agcagagcaa cctgcacaga    480
gtgctgatgg acctgcagaa ccagaagctg aaggagctga cgactggct gaccaagacc    540 gaggagcgga ccagaaagat ggaggaggag cccctgggcc cgacctgga ggacctgaag    600 agacaggtgc agcagcacaa ggagaccgag atcgccgtgc aggccaagca gcccgacgtg    660
gaggagatcc tgagcaaggg ccagcacctg tacaaggaga agcctgccac ccagcccgtg    720
aagagaaagc tggaggatct gagcagcgag tggaaggccg tgaacagact gctgcaggag    780
ctgagagcca acagcctga cctggcccct ggcctgacca ccatcggcgc cagccccacc    840
cagacagtga ccctggtgac ccagcctgtg gtgaccaagg agacagccat cagcaagctg    900
gagatgccca gctccctgat gctggaagtg cccgccctgg ccgatttcaa tagggcctgg    960
accgagctga ccgattggct gtccctgctg gaccaggtga tcaagagcca gagagtgatg   1020
gtgggcgatc tggaggacat caacgagatg atcatcaagc agaaagccac catgcaggac   1080
ctggagcaga ggagacccca gctggaagag ctgatcacag ccgcccagaa cctgaagaac   1140
aagaccagca accaggaggc caggaccatc atcaccgacc ggatcgagag gatccagaac   1200
cagtgggatg aagtgcagga acacctgcag aacagacggc agcagctgaa cgagatgctg   1260
aaggacagca cccagtggct ggaggccaag gaggaggccg agcaggtgct gggccaggcc   1320
agagccaagc tggagtcctg gaaggagggc ccttacaccg tggatgccat ccagaagaag   1380
atcaccgaga ccaagcagct ggccaaggac ctgagacagt ggcagaccaa cgtggacgtg   1440
gccaatgatc tggcccctgaa gctgctgaga gactacagcg ccgacgatac ccggaaagtg   1500
cacatgatca cagagaacat caatgcttct tggcggagca tccacaagag agtgagcgag   1560
agagaagccg ccctggaaga gactcatagg ctgctccagc agttccctct ggacctggag   1620
aagttcctgg cctggctgac agaggccgag accaccgcca acgtgctgca ggacgccacc   1680
agaaaggaga gactgctgga ggatagcaag ggcgtgaagg aactgatgaa gcagtggcag   1740
gatctgcagg gcgaaatcga ggcccacacc gacgtgtacc acaacctgga cgagaacagc   1800
cagaagatcc tgagaagcct ggagggcagc gacgacgccg tgctgctgca gagaaggctg   1860
gacaacatga acttcaagtg gagcgagctg cggaagaaga gcctgaacat ccggagccac   1920
ctggaagcca gcagcgacca gtggaagaga ctgcacctga gcctgcagga actgctggtg   1980
tggctgcagc tgaaggacga cgagctgagc agacaggccc ccatcggcgg cgacttcccc   2040
gccgtgcaga gcagaacga cgtgcaccgg gccttcaaga gggagctgaa aaccaaggaa   2100
cccgtgatca tgagcaccct ggagacagtg cggatcttcc tgaccgagca gccccctggag   2160 ggcctggaga agctgtacca ggagcccaga gagctgcccc cgaggagag agcccagaac   2220 gtgacccggc tgctgagaaa gcaggccgag gaagtgaata ccgagtggga aagctgaat   2280 ctgcactccg ccgactggca gagaaagatc gacgagaccc tggaacgcct gcaggagctg   2340
caggaagcca ccgacgagct ggacctgaaa ctgaggcagg ccgaagtgat caagggcagc   2400
tggcagcctg tgggcgacct gctgatcgat tccctgcagg accacctgga aaaagtgaag   2460
gccctcaggg gcgagatcgc tcctctgaag gagaatgtga gccacgtgaa cgacctggcc   2520
```

```
agacagctga ccaccctggg catccagctg agccoctaca acctgagcac actggaagat    2580
ctgaacaccc ggtggaagct gctgcaggtg gccgtggagg atagagtgag gcagctgcac    2640
gaagcccaca gagacttcgg ccctgccagc cagcacttcc tgagcaccag cgtgcagggc    2700
ccctgggaga gagccatctc ccccaacaaa gtgccctact acatcaacca cgagacccag    2760
accacctgct gggaccaccc taagatgacc gagctgtatc agagcctggc cgacctgaac    2820
aatgtgcggt tcagcgccta cagaaccgcc atgaagctgc ggagactgca gaaggccctg    2880
tgcctggacc tgctgagcct gagcgccgcc tgcgacgccc tggaccagca aacctgaag    2940 cagaatgacc agcccatgga catcctgcag atcatcaact gcctgaccac aatctacgat    3000
cggctggagc aggagcacaa caacctggtg aacgtgcccc tgtgcgtgga catgtgcctg    3060
aattggctgc tgaacgtgta cgacaccggc aggaccggca gaatcagagt gctgtccttc    3120
aagaccggca tcatcagcct gtgcaaggcc cacctggagg ataagtaccg ctacctgttc    3180
aagcaggtgg ccagcagcac cggcttctgc gatcagagga gactgggcct gctgctgcac    3240
gatagcatcc agatccctag gcagctgggc gaagtggcca gctttggcgg cagcaacatc    3300
gagccctctg tgaggagctg cttccagttc gccaacaaca gcccgagat cgaggccgcc    3360 ctgttcctgg attggatgag gctggagccc cagagcatgg tgtggctgcc tgtgctgcac    3420
agagtggccg ccgccgagac cgccaagcac caggccaagt gcaacatctg caaggagtgc    3480
cccatcatcg gcttccggta caggagcctg aagcacttca actacgacat ctgccagagc    3540
tgctttttca gcggcagagt ggccaagggc acaagatgc actacccat ggtgagtac    3600 tgcaccccca ccacctccgg cgaggatgtg agagacttcg ccaaagtgct gaagaataag    3660
ttccggacca gcggtactt tgccaagcac cccaggatgg gctacctgcc cgtgcagacc    3720
gtgctggagg gcgacaacat ggagaccgac accatgtgat gatga                   3765
```

<210> SEQ ID NO 7
<211> LENGTH: 3606
<212> TYPE: DNA
<213> ORGANISM: artificial
<220> FEATURE:
<223> OTHER INFORMATION: optimized delta R4-R23/delta CT

<400> SEQUENCE: 7

```
gccaccatgc tgtggtggga ggaagtggag gactgctacg agagagagga cgtgcagaag      60
aaaaccttca ccaagtgggt gaacgcccag ttcagcaagt tcggcaagca gcacatcgag     120
aacctgttca gcgacctgca ggatggcagg agactgctgg atctgctgga gggactgacc     180
ggccagaagc tgcccaagga agggcagc accagagtgc acgccctgaa caacgtgaac     240
aaggccctga gagtgctgca gaacaacaac gtggacctgg tgaatatcgg cagcaccgac     300
atcgtggacg gcaaccacaa gctgaccctg gcctgatct ggaacatcat cctgcactgg     360
caggtgaaga acgtgatgaa gaacatcatg gccggcctgc agcagaccaa cagcgagaag     420
atcctgctga gctgggtgag gcagagcacc agaaactacc cccaggtgaa cgtgatcaac     480
ttcaccacct cctggagcga cggcctggcc ctgaacgccc tgatccacag ccacagaccc     540
gacctgttcg actggaacag cgtggtgtgt cagcagagcg ccaccagag actggagcac     600 gccttcaaca tcgccagata ccagctgggc atcgagaagc tgctggaccc cgaggacgtg     660
gacaccacct accccgacaa gaaaagcatc ctgatgtata ttacctctct gtttcaggtg     720
ctgccccagc aggtgtccat cgaggccatc caggaagtgg aaatgctgcc caggcccccc     780
```

```
aaagtgacca aggaggagca cttccagctg caccaccaga tgcactatag ccagcagatc    840
accgtgtccc tggcccaggg ctatgagaga accagcagcc ccaagcccag attcaagagc    900
tacgcctaca cccaggccgc ctacgtgacc acctccgacc ccaccagaag ccccttcccc    960
agccagcacc tggaggcccc cgaggacaag agcttcggca gcagcctgat ggagagcgaa   1020
gtgaacctgg acagatacca gaccgccctg gaggaagtgc tgtcttggct gctgtccgcc   1080
gaggacaccc tgcaggccca gggcgagatc agcaacgacg tggaagtggt gaaggaccag   1140
ttccacaccc acgagggcta catgatggat ctgaccgccc accagggcag agtgggcaat   1200
atcctgcagc tgggcagcaa gctgatcggc accggcaagc tgagcgagga cgaggagacc   1260
gaagtgcagg agcagatgaa cctgctgaac agcagatggg agtgcctgag agtggccagc   1320
atggagaagc agagcaacct gcaccgcgtg ctgatggacc tgcagaacca gaagctgaag   1380
gagctgaacg actggctgac caagaccgag gagcggacca aaagatgga ggaggagccc   1440
ctgggccccg acctggagga cctgaagaga caggtgcagc agcacaaagt gctgcaggag   1500
gacctggaac aggagcaggt gcgcgtgaac agcctgaccc acatggtggt cgtggtggac   1560
gagagcagcg gcgaccacgc cacagccgcc ctggaagagc agctgaaagt gctgggcgac   1620
agatgggcca acatctgccg gtggaccgag gacagatggg tgctgctgca ggacatcctg   1680
ctgaagtggc agagactgac agaggagcag tgcctgtttta gcgcctggct gagcgagaag   1740
gaggacgccg tgaacaagat ccacaccacc ggcttcaagg accagaacga gatgctgagc   1800
agcctgcaga gctggccgt gctgaaggcc gatctggaga agaaaaagca gagcatgggc   1860
aagctgtact ccctgaagca ggacctgctg tccaccctga gaacaagag cgtgacccag   1920
aaaccgagg cctggctgga caatttcgcc cggtgctggg acaatctggt gcagaaactg   1980
gagaagagca ccgcccagat cagccaggcc gtgaccacca cccagcccag cctgacacag   2040
accaccgtga tggagaccgt gaccacagtg accaccaggg agcagatcct ggtgaagcac   2100
gcccaggagg agctgcccc tcccccccct cagaagaagc ggcagatcac agtggacacc   2160
ctggagagac tgcaggagct gcaggaagcc accgacgagc tggacctgaa gctgagacag   2220
gccgaagtga tcaagggcag ctggcagcct gtgggcgatc tgctgatcga cagcctgcag   2280
gaccacctgg agaaagtgaa ggccctgcgg ggcgagatcg cccccctgaa ggagaatgtg   2340
agccacgtga cgacctggc cagacagctg accaccctgg gcatccagct gagcccctac   2400
aatctgagca ccctggaaga tctgaacacc cggtggaaac tgctgcaggt ggccgtggag   2460
gatagagtga ggcagctgca cgaggcccac agagacttcg gccctgcctc ccagcacttc   2520
ctgagcacca gcgtgcaggg ccctgggag agagccatct ccccccaacaa agtgccctac   2580
tacatcaacc acgagaccca gaccacctgc tgggaccacc ctaagatgac cgagctgtac   2640
cagagcctgg ccgacctgaa caatgtgcgg ttcagcgcct acagaaccgc catgaagctg   2700
cggagactgc agaaggccct gtgcctggac ctgctgagcc tgagcgccgc ctgcgacgcc   2760
ctggaccagc acaacctgaa gcagaacgac cagcccatgg acattctgca gatcatcaac   2820
tgcctgacca ccatctacga tcggctggag caggagcaca caacctggt gaacgtgccc   2880
ctgtgcgtgg acatgtgcct gaattggctg ctgaacgtgt acgacaccgg caggaccggc   2940
agaatcagag tgctgtcctt caagaccggc atcatcagcc tgtgcaaggc ccacctggag   3000
gataagtacc gctacctgtt caagcaggtg ccagcagca ccggcttctg cgatcagagg   3060
agactggggc tgctgctgca cgatagcatc cagatcccta ggcagctggg cgaagtggcc   3120
agctttggcg gcagcaacat cgagccctct gtgaggagct gcttccagtt cgccaacaac   3180
```

```
                                            -continued aagcccgaga tcgaggccgc cctgttcctg gattggatga ggctggagcc ccagagcatg      3240
gtgtggctgc ctgtgctgca cagagtggcc gccgccgaga ccgccaagca ccaggccaag      3300
tgcaacatct gcaaggagtg ccccatcatc ggcttccggt acaggagcct gaagcacttc      3360
aactacgaca tctgccagag ctgcttttc agcggcagag tggccaaggg ccacaagatg       3420
cactacccca tggtggagta ctgcacccc accacctccg gcgaggatgt gagagacttc       3480
gccaaagtgc tgaagaataa gttccggacc aagcggtact ttgccaagca ccccaggatg     3540
ggctacctgc ccgtgcagac cgtgctggag ggcgacaaca tggagaccga caccatgtga      3600
tgatga                                                                 3606
```

COMBINED THERAPY FOR DUCHENNE MUSCULAR DYSTROPHY

SEQUENCE LISTING

The instant application contains a Sequence Listing which has been submitted electronically in ASCII format and is hereby incorporated by reference in its entirety. Said ASCII copy, created on Nov. 29, 2017, is named B2046PC00-SEQ_LIST_ST25 and is 10,763 bytes in size.

FIELD OF THE INVENTION

The present invention relates to the combined use of antisense oligonucleotides and viral vectors for the treatment of Duchenne muscular dystrophy.

BACKGROUND OF THE INVENTION

The dystrophinopathies are pathologies caused by anomalies in the DMD gene that encodes a subsarcolemmal protein called dystrophin. With regard to the large deletions, the most frequent genetic alteration, the severity of the phenotype is primarily conditioned by the impact of the mutation on the protein reading frame of the dystrophin transcript. Dystrophin is absent in Duchenne muscular dystrophy (DMD) due to mutations disrupting the open reading frame. In a milder form of the disease, Becker muscular dystrophy, mutations create shortened but in-frame transcripts that encode a partially functional dystrophin. The dystrophin structure (central rod-domain made of 24 spectrin-like repeats) tolerates large internal deletions (1) which led to the development of two main therapeutic strategies: classical gene therapy with transfer of functional micro-dystrophin cDNAs in muscles, and targeted exon skipping. Both approaches have shown encouraging results using adeno-associated viral (AAV) vectors, which allow efficient gene transfer into muscles. Exon skipping strategy converts an out-of-frame mutation into an in-frame mutation leading to an internally deleted but partially functional dystrophin. This therapeutic approach has demonstrated some success using antisense oligonucleotides (AONs), in particular in recent clinical studies (2-5). AONs have the enormous advantage of not being immunogenic but have the disadvantage of having to be regularly injected to maintain therapeutic benefit. We and others have shown that alternatively the antisense sequences could be introduced into skeletal or cardiac muscles using a small nuclear RNA such as U7snRNA or U1 snRNA (6-8). These therapeutic molecules are vectorised in AAV particles which ensure a permanent production of the therapeutic antisense in dystrophin-deficient murine models (7-9), as well as in the dystrophin-deficient dog GRMD (10; 11). A one-shot treatment of AAV-U7 is sufficient to attain substantial levels of restored quasi-dystrophin, which is associated with a significant improvement of the muscle force. AAV genome fate in dystrophic muscles is of importance considering the viral capsid immunogenicity that prohibits today recurring treatments (12). Since muscular dystrophies are characterized by repeated cycles of necrosis-regeneration and because AAV vectors display a non integrative episomal genome, we hypothesized that AAV-U7 could be lost during the necrosis of dystrophic myofibers. Indeed, we followed therapeutic viral genomes during AAV-U7-mediated exon skipping therapy in the severe dystrophic dKO mice and the GRMD dogs after optimal dystrophin rescue and showed that dystrophin restoration decreased significantly after one year in various skeletal muscles which was correlated with important viral genome loss (13; 11). Importantly, we showed that the moderately dystrophic mdx muscles lose non therapeutic viral genomes quickly after the injection and that this loss is strongly slowed down when high doses of viral genomes restore dystrophin quickly at the sarcolemma (13). Importantly, no similar rapid loss of AAV genomes is observed from normal control muscle. Therefore, we previously proposed, to achieve long-term restoration of dystrophin expression, a two-step treatment with firstly, a single systemic injection of AAV-U7 vector to induce a strong and widespread expression of dystrophin in muscles, and secondly, recurrent systemic injections of antisense oligonucleotides to prevent the progressive reappearance of a dystrophic phenotype caused by the partial loss of AAV genomes over time (13). However, improved methods for long-term restoration of dystrophin expression are still needed.

SUMMARY OF THE INVENTION

In a first aspect, the present invention relates to an isolated antisense oligonucleotide (AON) capable of inducing an exon-skipping in a dystrophin pre-mRNA, for use in the treatment of a muscular dystrophy in combination with a viral vector coding a muscular dystrophy therapeutic product, which may be, for example, either (i) an antisense oligonucleotide capable of inducing an exon-skipping in a dystrophin pre-mRNA or (ii) a viral vector coding a functional dystrophin protein, wherein said treatment comprises administering said oligonucleotide before administering said viral vector.

In a second aspect, the present invention relates to an isolated AON capable of inducing an exon-skipping in a dystrophin pre-mRNA, for use in the treatment of a muscular dystrophy, wherein said AON is administered as a pretreatment before administration to the patient in need thereof of a therapeutic viral vector, such as a viral vector coding an antisense oligonucleotide capable of inducing an exon-skipping in a dystrophin pre-mRNA, or a viral vector carrying a functional dystrophin-coding gene.

In a third aspect, the invention relates to a kit comprising (i) an isolated AON capable of inducing an exon-skipping in a dystrophin pre-mRNA and (ii) a viral vector coding an antisense oligonucleotide capable of inducing an exon-skipping in a dystrophin pre-mRNA, or a viral vector carrying a functional dystrophin-coding gene. The kit of the present invention is useful for implementing the therapeutic methods described herein.

DETAILED DESCRIPTION OF THE INVENTION

The present inventors herein show that a two-step combination therapy of a muscular dystrophy is advantageous over treatment strategies known in the prior art. The invention relates to an isolated antisense oligonucleotide as described above, appropriate for inducing exon-skipping within a dystrophin pre-mRNA and inducing muscle cells to produce an mRNA transcript that encodes a functional dystrophin protein, for use in a method for the treatment of Duchenne muscular dystrophy, wherein said isolated AON secures muscle cell integrity before an intended viral vector Duchenne muscular dystrophy therapy. The combination therapy proposed herein first comprises the administration of an isolated AON as described above, appropriate for inducing exon-skipping within a dystrophin pre-mRNA and inducing muscle cells to produce an mRNA transcript that encodes a functional dystrophin protein. In a second step, the method of the present invention comprises administering to the same subject at least one viral vector encoding a Duchenne muscular dystrophy therapeutic product. The viral vector (or therapeutic viral vector) is designed for restoring a dystrophin function in a muscle cell. For example, the at least one viral vector able to restore a dystrophin function in the muscle cell is a viral vector either (i) coding for an antisense oligonucleotide (which is also referred to as "AON-coding virus" in the following description) able to induce exon-skipping within a dystrophin pre-mRNA and inducing muscle cells to produce an mRNA transcript that encodes a functional dystrophin protein, (ii) designed to introduce into the muscle cell means for correcting the dystrophin gene in the genome of said muscle cell, such as genome-editing means implementing one or more endonucleases specific for the dystrophin gene, or (iii) coding a functional dystrophin protein.

Without wishing to be bound to any particular theory, it is believed that the period of time between AON-coding virus injection and the expression of a functional dystrophin (either by way of exon-skipping within an endogenous dystrophin pre-mRNA or by way of expressing an heterologous dystrophin gene) in sufficient quantity at the sarcolemma is critical for the maintenance of the therapeutic viral genomes in the treated muscles. For this reason, it is believed that a first step of inducing temporary functional dystrophin expression at the sarcolemma of myofibers with isolated AONs secures membrane integrity before injection of a therapeutic viral vector able to restore dystrophin function in a muscle cell. This could be particularly critical for recombinant AAV vectors that display a non integrative episomal genome, and that might be lost during the repeated cycles of necrosis-regeneration which is one of the features of dystrophic myofibers.

The term "antisense oligonucleotide" and "AON" are used interchangeably and refer to a single stranded nucleic acid sequence, e.g. a DNA or RNA sequence, which is complementary to a part of a pre-mRNA coding the dystrophin protein and is thus able to form, by Watson-Crick base pairing, to a heteroduplex within the target sequence. In particular, the AON of the present invention is designed to block a splice acceptor (SA) site and/or an exon splicing enhancer (ESE) and/or a branch point in the dystrophin pre-mRNA and/or a splice donor (SD) site and/or any sequence which could modulate pre-mRNA splicing, i.e. it is designed to be complementary to a part of the dystrophin pre-mRNA comprising an SA, an ESE, a branch point sequence, an SD, and/or any sequence which could modulate pre-mRNA splicing (14,15).

In a particular embodiment, the targeted sequence within the dystrophin pre-mRNA may include a 3' or 5' splice site of a pre-mRNA, or a branch point. The target sequence may be within an exon or within an intron or overlapping an intron-exon or exon-intron junction. The target sequence for a splice site may include an mRNA sequence having its 5' end 1 to about 50 base pairs downstream of a normal splice acceptor junction in a preprocessed mRNA. A preferred target sequence for a splice is any region of a pre-mRNA that includes a splice site and/or is contained entirely within an exon coding sequence and/or spans a splice acceptor and/or donor site. Of course, the target sequence may include several of these sequences that can modulate pre-mRNA splicing, and several such target sequences can be combined to achieve the desired effect.

Tools are available for identifying SA, ESE, SD and branch point sequences in a pre-mRNA of interest. As is well known by those skilled in the art, SA are conserved sequences, they are at the 3' end of the intron and terminate the intron with an almost invariant AG sequence. SD are conserved sequences, they are at the 5' end of the intron and start the intron with an almost invariant GT sequence. In addition, ESE motifs may be predicted on the exon sequence intended to be skipped using the ESEfinder software tool (http://rulai.cshl.edu/cgi-bin/tools/ESE3/esefinder.cgi?process=home). Design of the AON can then be carried out following the rules published in Aartsma-Rus et al. (16).

The AON of the invention is designed to complement suitable sequences within the dystrophin pre-mRNA which are required for correct splicing of the targeted exon, thereby blocking splicing reactions that would incorporate the targeted exon into mature mRNA.

The mutated human dystrophin genes express no measurable dystrophin at all in muscles of Duchenne muscular dystrophy patients. To remedy this condition, the antisense oligonucleotides of the present invention typically hybridize to selected regions of a pre-mRNA of a mutated human dystrophin gene, induce exon skipping in dystrophin mRNA, and thereby allow muscle cells to produce an mRNA transcript that encodes a functional dystrophin protein. Exon skipping strategy converts an out-of-frame mutation into an in-frame mutation leading to an internally deleted but partially functional dystrophin. Therefore, depending on the skipped exon(s), the rescued proteins will at best improve dystrophic phenotypes toward milder Becker-like phenotypes. In certain embodiments, the resulting dystrophin protein is not necessarily the "wild-type" form of dystrophin, but is rather a truncated, yet functional or semi-functional, form of dystrophin. By increasing the levels of functional dystrophin protein in muscle cells, these and related embodiments may be useful in the prophylaxis and treatment of Duchenne muscular dystrophy. The combined therapy described herein provides significant and practical advantages over alternate methods of treating Duchenne muscular dystrophy.

"Exon skipping" refers generally to the process by which an entire exon, or a portion thereof, is removed from a given pre-mRNA, and is thereby excluded from being present in the mature mRNA. Hence, the portion of the protein that is otherwise encoded by the skipped exon is not present in the expressed form of the protein, typically creating an altered, though still functional, form of the protein. In certain embodiments, the exon being skipped is an aberrant exon from the human dystrophin gene, which may contain a mutation or other alteration in its sequence. In certain embodiments, the exon being skipped is any one or more of exons 1-79 of the dystrophin gene, though any one or more of exons 23, 43, 44, 45, 46, 47, 48, 49, 50, 51, 52, 53, 54, and/or 55 of the human dystrophin gene are preferred. Depending of the localization of the DMD patient mutation, one or several exons are chosen to be skipped to restore the dystrophin coding frame leading to an internally deleted but partially functional dystrophin. "Dystrophin" is a rod-shaped cytoplasmic protein, and a vital part of the protein complex that connects the cytoskeleton of a muscle fiber to the surrounding extracellular matrix through the cell membrane. Dystrophin contains multiple functional domains. For instance, dystrophin contains an actin binding domain at about amino acids 14-240 and a central rod domain at about amino acids 253-3040. This large central domain is formed by 24 spectrin-like triple-helical elements of about 109 amino acids, which have homology to alpha-actinin and spectrin. The repeats are typically interrupted by four proline-rich non-repeat segments, also referred to as hinge regions. Repeats 15 and 16 are separated by an 18 amino acid stretch that appears to provide a major site for proteolytic cleavage of dystrophin. The sequence identity between most repeats ranges from 10-25%. One repeat contains three alpha-helices: 1, 2 and 3. Alpha-helices 1 and 3 are each formed by 7 helix turns, probably interacting as a coiled-coil through a hydrophobic interface. Alpha-helix 2 has a more complex structure and is formed by segments of four and three helix turns, separated by a Glycine or Proline residue. Each repeat is encoded by two exons, typically interrupted by an intron between the nucleic acid position coding amino acids 47 and 48 in the first part of alpha-helix 2. The other intron is found at different positions in the repeat coding region, usually scattered over helix-3. Dystrophin also contains a cystein-rich domain at about amino acids 3080-3360), including a cystein-rich segment (i.e., 15 Cysteins in 280 amino acids) showing homology to the C-terminal domain of the slime mold (Dictyostelium discoideum) alpha-actinin. The carboxy-terminal domain is at about amino acids 3361-3685.

The amino-terminus of dystrophin binds to F-actin and the carboxy-terminus binds to the dystrophin-associated protein complex (DAPC) at the sarcolemma. The DAPC includes the dystroglycans, sarcoglycans, integrins and caveolin, and mutations in any of these components cause autosomally inherited muscular dystrophies. The DAPC is destabilized when dystrophin is absent, which results in diminished levels of the member proteins, and in turn leads to progressive fibre damage and membrane leakage. In various forms of muscular dystrophy, such as Duchenne's muscular dystrophy (DMD) and Becker's muscular dystrophy (BMD), muscle cells produce an altered and functionally defective form of dystrophin, or no dystrophin at all, mainly due to mutations in the gene sequence. The predominant expression of the defective dystrophin protein, or the complete lack of dystrophin or a dystrophin-like protein, leads to rapid progression of muscle degeneration, as noted above. In this regard, a "defective" dystrophin protein may be characterized by the forms of dystrophin that are produced in certain subjects with DMD or BMD, as known in the art, or by the absence of detectable dystrophin.

As used herein, the terms "function" and "functional" and the like refer to a biological, enzymatic, or therapeutic function. A "functional" dystrophin protein refers generally to a dystrophin protein having sufficient biological activity to reduce the progressive degradation of muscle tissue that is otherwise characteristic of muscular dystrophy, typically as compared to the altered or "defective" form of dystrophin protein that is present in certain subjects with DMD or BMD. In certain embodiments, a functional dystrophin protein may have about 10%, 20%, 30%, 40%, 50%, 60%, 70%, 80%, 90%, or 100% (including all integers in between) of the in vitro or in vivo biological activity of wild-type dystrophin, as measured according to routine techniques in the art. As one example, dystrophin-related activity in muscle cultures in vitro can be measured according to myotube size, myofibril organization (or disorganization), contractile activity, and spontaneous clustering of acetylcholine receptors (17). Animal models are also valuable resources for studying the pathogenesis of disease, and provide a means to test dystrophin-related activity. Two of the most widely used animal models for DMD research are the mdx mouse and the golden retriever muscular dystrophy (GRMD) dog, both of which are dystrophin negative (see, e.g., Collins & Morgan, Int J Exp Pathol 84: 165-172, 2003). These and other animal models can be used to measure the functional activity of various dystrophin proteins. Included are truncated forms of dystrophin, such as those forms that are produced by certain of the exon-skipping antisense compounds of the present invention.

The isolated AON of the invention may be of any suitable type. Representative AON types include oligodeoxyribonucleotides, oligoribonucleotides, morpholinos (such as phosphorodiamidate morpholino (PMO) or peptide-phosphorodiamidate morpholino (PPMO)), 2'-O-methyl-phosphorothioate (2'OMePS), 2'-O-2-methoxyethyl-antisense oligonucleotides, tricyclo-DNA-antisense oligonucleotides, tricyclo-phosphorothioate DNA oligonucleotides, LNA, small nuclear RNA-modified such as U7-, U1- or U6-modified AONs (or other UsnRNPs), or conjugate products thereof such as peptide-conjugated or nanoparticle-complexed AONs.

In particular, for use in vivo, the AONs may be stabilized, for example via phosphate backbone modifications. For example, stabilized AONs of the instant invention may have a modified backbone, e.g. have phosphorothioate linkages. Other possible stabilizing modifications include phosphodiester modifications, combinations of phosphodiester and phosphorothioate modifications, methylphosphonate, methylphosphorothioate, phosphorodithioate, p-ethoxy, and combinations thereof. Chemically stabilized, modified versions of the AONs also include "Morpholinos" (phosphorodiamidate morpholino oligomers, PMOs), 2'-O-Methyl oligomers, tricyclo-DNAs, tricyclo-DNA-phosphorothioate AON molecules (WO2013/053928) or U small nuclear (sn) RNAs. The latter forms of AONs that may be used to this effect can be coupled to small nuclear RNA molecules such as U1, U6 or U7 (or other UsnRNPs).

In a particular embodiment, the isolated AON used in the present invention is a 2'OMePS oligonucleotide or a PPMO oligonucleotide. Preferably, the AON is a PPMO oligonucleotide.

AONs employed in the practice of the invention are generally from about 10 to about 40 nucleotides in length, and may be for example, about 10, or about 15, or about 20, or about 25, or about 30, or about 35, or about 40 nucleotides or more in length depending on the targeted sequences within the dystrophin pre-mRNA and the AON chemistry.

A representative AON for practice of the invention may be GGCCAAACCTCGGCTTACCTGAAAT (SEQ ID NO:1), effecting exon 23 skipping of mouse dystrophin pre-mRNA.

Of course, any AON having the properties described above may be used in the practice of the present invention.

In an embodiment, the isolated AON of the invention has the sequence shown in SEQ ID NO:1 and is a PPMO oligonucleotide.

For stable and efficient in vivo delivery, the isolated AONs used in the practice of the present invention may also be fused or co-administered to any cell-penetrating peptides and to signal peptides mediating protein secretion. Cell-penetrating peptides can be RVG peptides (18), PiP (19) such as Pip6a-PMO (20), P28 (21), or protein transduction domains like TAT (22) or VP22 (23). In a particular embodiment, the isolated AON is a PPMO oligonucleotide, i.e. a PMO oligonucleotide fused to a peptide moiety, more particularly a Pip6a-PMO, even more particularly a Pip6a-PMO. In a particular embodiment, the PPMO oligonucleotide moiety comprises or consists of the sequence shown in SEQ ID NO:1. In a further particular embodiment, the isolated AON is a Pip6a-PMO whose oligonucleotide moiety comprises or consists of the sequence shown in SEQ ID NO:1.

Furthermore, the isolated AON used in the practice of the invention may be administered as a composition further comprising a pharmaceutically acceptable carrier and a reagent that improves oligonucleotide delivery efficiency. Such reagent may include, without limitation, F127 (24).

In a particular embodiment of the invention, the isolated AON of the invention is capable of inducing functional dystrophin expression of at least 10%, preferably of at least 20%, preferably of at least 30%, preferably of at least 40%, preferably 50%, more preferably at least 51%, 52%, 53%, 54%, 55% or at least 56%, as compared to the normal expression level of wild-type dystrophin. Of course, higher functional dystrophin expression is also preferable, such as an expression of at least 60%, 70%, 80% or even of at least 90%, as compared to the normal expression level of wild-type dystrophin.

In the second step of the method invention, a viral vector coding a therapeutic product is also administered to the same patient in need of the treatment. In the context of the present invention, the therapeutic product is able to restore a dystrophin function in a muscle cell in need thereof.

In a particular embodiment, the viral vector coding a therapeutic product is an AON-coding virus. The AON coded by this virus is as defined above, and is able to induce exon-skipping within a dystrophin pre-mRNA and to induce muscle cells to produce an mRNA transcript that encodes a functional dystrophin protein.

In another specific embodiment, the viral vector, or several viral vectors, encodes means for correcting the dystrophin gene in the genome of a muscle cell. In this embodiment, the viral vector able to restore dystrophin function in a muscle cell is designed for correcting a mutant dystrophin gene in a subject by introducing into the genome of said cell a genome-editing system. For example, a site-specific nuclease may be encoded by the viral vector, which may restore the expression of a full-functional or partially-functional dystrophin protein with a repair template or donor DNA, which can replace the entire dystrophin gene or the region containing the mutation. The site-specific nuclease may be used to introduce site-specific double strand breaks at targeted genomic loci. Site-specific double-strand breaks are created when the site-specific nuclease binds to a target DNA sequence, thereby permitting cleavage of the target DNA. This DNA cleavage may stimulate the natural DNA-repair machinery, leading to one of two possible repair pathways: homology-directed repair (HDR) or the non-homologous end joining (NHEJ) pathway. This embodiment may comprise introducing into the muscle cell a genome-editing means implementing one or more endonucleases (for example one or more meganuclease(s), TALEN(s), ZFN(s) or a CRISPR/Cas9 endonuclease) specific for the dystrophin gene and one or more repair matrices. Such systems are described and known to those skilled in the art, for example in WO11036640, WO13163628, WO14009567 and WO14197748.

In another embodiment, the therapeutic product coded by the viral vector is a functional dystrophin. As mentioned above, a "functional" dystrophin protein refers generally to a dystrophin protein having sufficient biological activity to reduce the progressive degradation of muscle tissue that is otherwise characteristic of muscular dystrophy, typically as compared to the altered or "defective" form of dystrophin protein that is present in certain subjects with DMD or BMD. In certain embodiments, a functional dystrophin protein may have about 10%, 20%, 30%, 40%, 50%, 60%, 70%, 80%, 90%, or 100% (including all integers in between) of the in vitro or in vivo biological activity of wild-type dystrophin, as measured according to routine techniques in the art. The functional dystrophin protein may be a truncated dystrophin protein, such as a mini- or micro-dystrophin. Such mini- and micro-dystrophin are known in the art, for example in WO02/29056, WO01/83695, WO08/088895 and Foster et al., 2008 (37). In a particular embodiment, the micro-dystrophin is a $\Delta AB/R3$-R18/$\Delta CT$ or $\Delta R4$-R23/$\Delta CT$ micro-dystrophin (more particularly a $\Delta R4$-R23/$\Delta CT$ micro-dystrophin), such as the $\Delta AB/R3$-R18/$\Delta CT$ or $\Delta R4$-R23/$\Delta CT$ micro-dystrophin described in Foster et al., 2008, more particularly the $\Delta R4$-R23/$\Delta CT$ micro-dystrophin. In a further particular embodiment, the mini- or micro-dystrophin coding gene is codon-optimized. In a further particular embodiment, the mini- or micro-dystrophin coding gene is codon optimized and encodes the $\Delta AB/R3$-R18/$\Delta CT$ or $\Delta R4$-R23/$\Delta CT$ micro-dystrophin, in particular the $\Delta R4$-R23/$\Delta CT$ micro-dystrophin described in Foster et al., 2008. The corresponding coding sequences are shown in SEQ ID NO: 6 and 7 respectively.

Adeno-associated viral vector (AAV)-mediated delivery of microdystrophins into dystrophin-deficient mice with DMD has shown remarkable efficiency (25, 26, 27) which has led to the initiation of an early-phase clinical trial (28).

Viral vectors include, but are not limited to, non-integrating viral vectors (or vectors integrating the genome of the target cell with low efficacy) such as episomally-maintained vectors, including adenoviruses; parvoviruses such as adeno-associated viruses; SV40-type viruses. One can readily employ other vectors not named but known in the art. Among the vectors that have been validated for clinical applications and that can be used to deliver the antisense sequences AAVs show a greater potential for exon skipping strategy.

In a preferred embodiment, the viral vector is a parvovirus, in particular an AAV vector. The parvovirus Adeno-Associated Virus (AAV) is a dependovirus that is naturally defective for replication and which is able to integrate into the genome of the infected cell to establish a latent infection. The last property appears to be unique among mammalian viruses because the integration occurs at a specific site in the human genome, called AAVS1, located on chromosome 19 (19q13.3-qter). AAV-based recombinant vectors lack the Rep protein and integrate with low efficacy and are mainly present as stable circular episomes that can persist for months and maybe years in the target cells. Therefore AAV has aroused considerable interest as a potential vector for human gene therapy. Among the favorable properties of the virus are its lack of association with any human disease and the wide range of cell lines derived from different tissues that can be infected. Actually 12 AAV serotypes (AAV1 to 12) and up to 120 variants are known (29; 30), each with different tissue tropisms. Accordingly, the present invention relates to an AAV vector coding the AON described above, targeting a dystrophin pre-mRNA and adapted to induce exon-skipping in said human pre-mRNA and to induce the production of a functional dystrophin protein in muscle cells. According to a particular embodiment, the AAV genome is derived from an AAV1, 2, 3, 4, 5, 6, 7, 8, 9, 10, 11 or 12 serotype. In a preferred embodiment, the AAV capsid is derived from an AAV1, 2, 3, 4, 5, 6, 7, 8, 9, 10, 11 or 12 serotype or AAV variants. In a further particular embodiment, the AAV vector is a pseudotyped vector, i.e. its genome and capsid are derived from AAVs of different serotypes. For example, the pseudotyped AAV vector may be a vector whose genome is derived from the AAV2 serotype, and whose capsid is derived from the AAV1, 3, 4, 5, 6, 7, 8, 9, 10, 11 or 12 serotype AAVs or AAV variants.

In addition, the genome of the AAV vector may either be a single stranded or self-complementary double-stranded genome (31). Self-complementary double-stranded AAV vectors are generated by deleting the terminal resolution site (trs) from one of the AAV terminal repeats. These modified vectors, whose replicating genome is half the length of the wild type AAV genome have the tendency to package DNA dimers.

Preferably, the AAV vector implemented in the practice of the present invention is a vector targeting muscle cells. In particular, AAV1, 6, 8 and 9 exhibit a high tropism for striated muscles (Zincarelli Mol Ther. 2008; Schultz Mol Ther. 2008) and are particularly preferred. In a preferred embodiment, the AAV vector has an AAV1, 6, 8 or 9 capsid, this vector being optionally pseudotyped.

In a particular embodiment, the AON coded by the AON-coding vector as described above is linked to a small nuclear RNA molecule such as a U1, U2, U6, U7 or any other small nuclear RNA (snRNA), or chimeric small nuclear RNA (32; 33). Information on U7 modification can in particular be found in Goyenvalle, et al. (34); WO2011/113889; and WO2006/021724. In a particular embodiment, the U7 cassette described by D. Schumperli is used (35). It comprises the natural U7-promoter (position −267 to +1), the U7smOpt snRNA and the downstream sequence down to position 116. The 18 nt natural sequence complementary to histone pre-mRNAs in U7 snRNA is replaced by one or two (either the same sequence used twice, or two different sequences) or more repeats of the selected AON sequences using, for example, PCR-mediated mutagenesis, as already described (34).

In a particular embodiment, the U7-modified AON comprises the sequence shown in SEQ ID NO:2:

(SEQ ID NO: 2)
GGCCAAACCTCGGCTTACCTAAATAGAAGTTCATTTACACTAAC.

In a particular embodiment, the small nuclear RNA-modified AONs, in particular the U7-modified AONs, are vectorized in an AAV vector.

Typically, the viral vector, notably the functional dystrophin-coding vector or the AON-coding vector may also comprise regulatory sequences allowing expression of the encoded functional dystrophin or AONs, such as e.g., a promoter, enhancer internal ribosome entry sites (IRES), sequences encoding protein transduction domains (PTD), and the like. In this regard, the vector most preferably comprises a promoter region, operably linked to the coding sequence, to cause or improve expression of the AON.

Such a promoter may be ubiquitous, tissue-specific, strong, weak, regulated, chimeric, etc., to allow efficient and suitable production of the AON. The promoter may be a cellular, viral, fungal, plant or synthetic promoter. Most preferred promoters for use in the present invention shall be functional in muscle cells. Non-limiting examples of muscle-specific promoters include the desmin promoter, the C5-12 synthetic promoter and the muscle creatine kinase (MCK) promoter. For its aspect relating to the expression of an AON, promoters may be selected from small nuclear RNA promoters such as U1, U2, U6, U7 or other small nuclear RNA promoters, or chimeric small nuclear RNA promoters. Other representative promoters include RNA polymerase III-dependent promoters, such as the H1 promoter, or RNA polymerase II-dependent promoters. Examples of regulated promoters include, without limitation, Tet on/off element-containing promoters, rapamycin-inducible promoters and metallothionein promoters. Examples of ubiquitous promoters include viral promoters, particularly the CMV promoter, the RSV promoter, the SV40 promoter, hybrid CBA (Chicken beta actin/CMV) promoter, etc. and cellular promoters such as the PGK (phosphoglycerate kinase) or EF1alpha (Elongation Factor 1 alpha) promoters.

The invention also relates to a composition comprising the isolated AON or the viral vector, as described above, in a pharmaceutically acceptable carrier. In addition to the AON or to the virus, a pharmaceutical composition of the present invention may also include a pharmaceutically or physiologically acceptable carrier such as saline, sodium phosphate, etc. The composition will generally be in the form of a liquid, although this need not always be the case. Suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, mineral oil, etc. The formulation can also include lubricating agents, wetting agents, emulsifying agents, preservatives, buffering agents, etc. In particular, the present invention involves the administration of an isolated AON or AON-coding virus and is thus somewhat akin to gene therapy. Those of skill in the art will recognize that nucleic acids are often delivered in conjunction with lipids (e.g. cationic lipids or neutral lipids, or mixtures of these), frequently in the form of liposomes or other suitable micro- or nano-structured material (e.g. micelles, lipocomplexes, dendrimers, emulsions, cubic phases, etc.).

The compositions of the invention are generally administered via enteral or parenteral routes, e.g. intravenously (i.v.), intra-arterially, subcutaneously, intramuscularly (i.m.), intracerebrally, intracerebroventricularly (i.c.v.), intrathecally (i.t.), intraperitoneally (i.p.), although other types of administration are not precluded.

Injectable preparations, for example, sterile injectable aqueous or oleaginous suspensions may be formulated according to the known art using suitable dispensing or wetting agents and suspending agents. The sterile injectable preparation can also be a sterile injectable solution or suspension in a nontoxic parenterally acceptable diluent or solvent, for example, as a solution in 1,3-butanediol. While delivery may be either local (i.e. in situ, directly into tissue such as muscle tissue) or systemic, usually delivery will be local to affected muscle tissue, e.g. to skeletal muscle, smooth muscle, heart muscle, etc. Depending on the form of the AON or the viral vector that is administered and the tissue or cell type that is targeted, techniques such as electroporation, sonoporation, a "gene gun" (delivering nucleic acid-coated gold particles), etc. may be employed.

One skilled in the art will recognize that the amount of an isolated AON or of a viral vector to be administered will be an amount that is sufficient to induce amelioration of unwanted muscular dystrophy symptoms. Such an amount may vary inter alia depending on such factors as the gender, age, weight, overall physical condition of the patient, etc. and may be determined on a case by case basis. The amount may also vary according to other components of a treatment protocol (e.g. administration of other medicaments, etc.). Generally, a suitable dose is in the range of from about 1 mg/kg to about 100 mg/kg, and more usually from about 2 mg/kg/day to about 10 mg/kg. In the case of viral-based delivery of AON, suitable doses will depend on different factors such as the virus that is employed, the route of delivery (intramuscular, intravenous, intra-arterial or other), but may typically range from 10e9 to 10e15 viral particles/ kg. Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient may be a single event, or the patient is administered with the AON and/or the viral vector on multiple occasions, that may be, depending on the results obtained, several days apart, several weeks apart, or several months apart, or even several years apart.

The present invention thus relates to the treatment of Duchenne muscular dystrophy, comprising a two-step administration of:

first an isolated antisense oligonucleotide which is complementary to a part of the dystrophin pre-mRNA and is able to induce exon-skipping during processing of this pre-mRNA to a mRNA; and secondly, a viral vector encoding a Duchenne muscular dystrophy therapeutic product, such as either (i) coding an antisense oligonucleotide able to induce exon-skipping within a dystrophin pre-mRNA, (ii) encoding dystrophin gene-editing means, or (iii) coding a functional dystrophin.

In a particular embodiment, the therapeutic product is an U7-modified AON, in particular an U7-modified AON comprising the sequence shown in SEQ ID NO:2, targeting exon 23 of the dystrophin gene.

As described above, it is believed that the first administration of the isolated AON induces sufficient functional dystrophin expression in muscle cells to secure membrane integrity and therefore limits loss of viral vectors, in particular AON-coding viruses (e.g. AAVs), dystrophin-correcting viruses (e.g. AAVs), or functional dystrophin-coding viruses (e.g. AAVs), due to otherwise repeated cycles of necrosis-regeneration of the dystrophic myofiber.

The time period between the injection of the isolated AON and the viral vector may vary depending on a number of factors, such as the stage of the disease, the age or condition of the patient, and the dosage of the therapy. In any event, the time between the first and second steps of the present method is sufficient for providing a long-lasting benefit of the viral vector treatment. The present method allows the maintenance of high viral therapeutic genome content and improved transgene expression in dystrophic muscles. The consequences of these initial events are a therapeutic benefit stronger of the AAV based therapy lasting longer than the non-combined therapy. Accordingly, the time between the first and second step of the method of the invention may be of from 1 to 40 days, such as at least one or more days, such of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 days; or of at least one or more weeks, such as at least 1, 2, 3, 4 or 5 weeks. In a particular embodiment, the time period between both administrations is of two weeks (i.e. of about 12 to 16 days, such as of about 12, 13, 14, 15 or 16 days), about three weeks (i.e. of about 19 to 23 days, such as of about 19, 20, 21, 22 or 23 days) or about four weeks (i.e. of about 26-30 days, such as of about 26, 27, 28, 29 or 30 days). More particularly, this time period is comprised between 14 and 28 days, and is more particularly of 12, 13, 14, 15, 16, 17, 18, 19, 20, 21, 22, 23, 24, 25, 26, 27 or 28 days. In another embodiment, the time period between both administrations is of about 14 (i.e 13, 14 or 15 days, more specifically 14 days), 21 (i.e 20, 21 or 22 days, more specifically 21 days) or 28 days (i.e 27, 28 or 29 days, more specifically 28 days).

Further aspects and advantages of the present inventions will be disclosed in the following experimental section, which shall be considered as illustrative only, and not limiting the scope of this application.

LEGEND OF THE FIGURES

FIG. 1. Viral genomes are efficiently maintained in Pip6a-PMO rescued mdx muscles (a) TAs from mdx and wt mice were injected with 1 nmole of Pip6a-PMO two weeks (−2 w) before the injection of 1E+11 vg of the non-therapeutic AAV1-U7scr vector (day 0, d0). Control mdx and wt TAs were injected with AAV1-U7scr vector alone. Four TAs were injected per group. The mice were sacrificed 3 weeks later (3 w). (b) Dystrophin rescue monitored by immunostaining with the NCL-DYS2 monoclonal antibody on transverse sections of TA muscles. One representative immunostained section is shown per condition. (c) Dystrophin restoration evaluated by western blotting with NCL-DYS1 monoclonal antibodies (upper panel) on whole protein extracts from the PPMO-treated muscles (lower panel: α-actinin). Dystrophin restoration was quantified by ImageJ software and expressed as the percentage of dystrophin expression in wt muscle. (d) Quantification of AAV genomes by absolute Taqman qPCR. AAV genome content is expressed as the AAV genome number relative to the value obtained for the non PPMO-treated mdx muscles. The data represent the mean values of 4 muscles per group ±SEM. n.s.: non-significant, ***$p<0.001$, Student's t-test. One of two representative experiments is shown.

Figure 2:
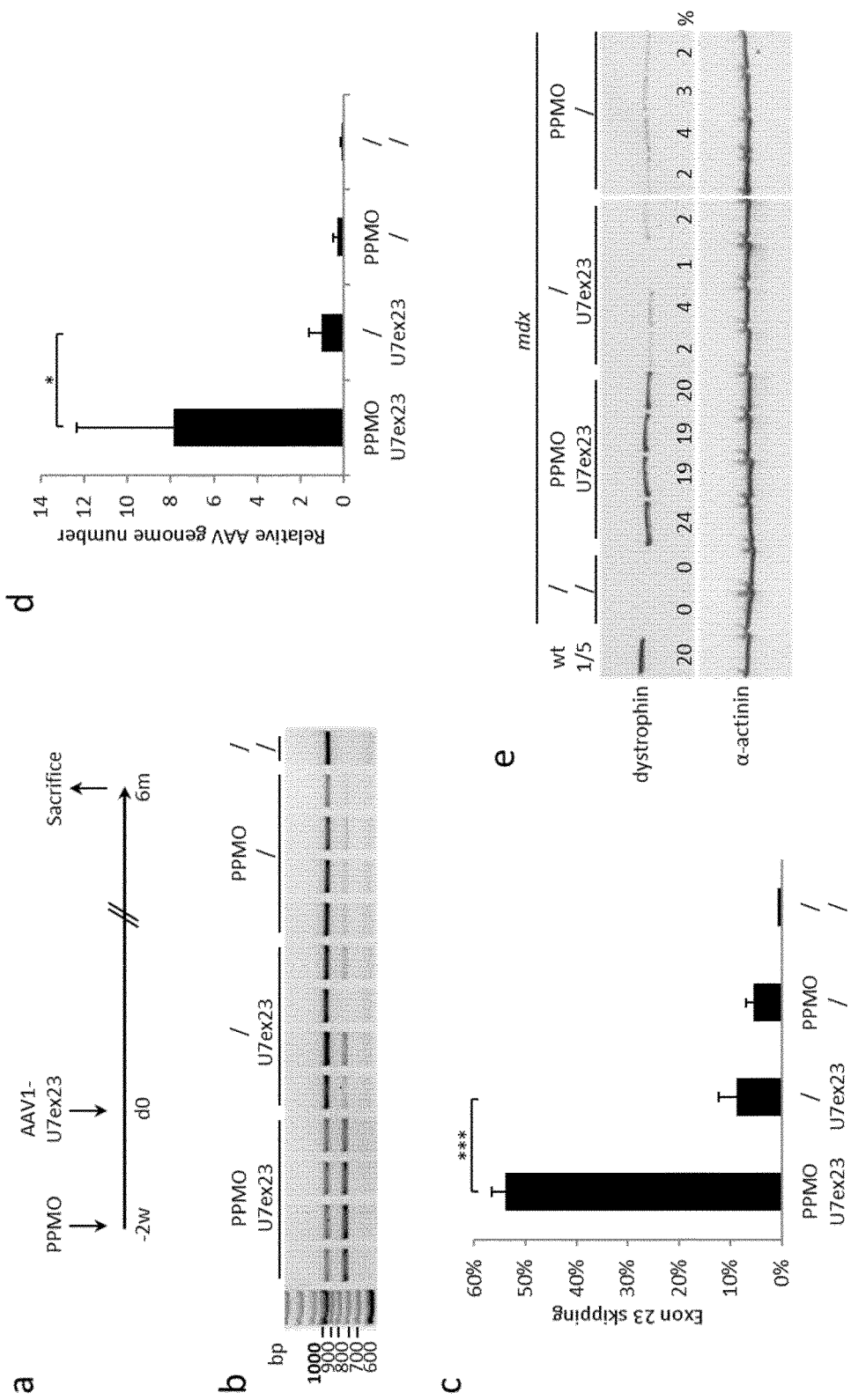

FIG. 2. Pip6a-PMO pre-treatment allows important dystrophin rescue at low AAV-U7ex23 close after 6 months (a) Mdx TAs were injected with 1 nmole of Pip6a-PMO two weeks (−2 w) before the injection of 1E+10 vg of therapeutic AAV1-U7ex23 vector (day 0, d0). Control mdx TAs were injected with PPMO or AAV1-U7ex23 vector alone. Four TAs were injected per group. The mice were sacrificed 6 months later (6 m). (b) Level of exon 23 skipping estimated by nested RT-PCR. The 901 bp PCR product corresponds to full-length dystrophin transcripts whereas the 688 bp product corresponds to transcripts lacking exon 23. (c) Quantification of exon 23 skipping performed by relative TaqMan qPCR and expressed as a percentage of total dystrophin transcripts. (d) Quantification of AAV genomes by absolute Taqman qPCR. AAV genome content is expressed as the AAV genome number relative to the value obtained for the non PPMO-treated mdx muscles. The data presented in (c) and (d) represent the mean values of the four TAs per group ±SEM. *$p<0.05$, ***$p<0.001$, Student's t-test. (e) Dystrophin restoration evaluated by western blotting with NCL-DYS1 monoclonal antibodies (upper panel) on whole protein extracts from the treated muscles (lower panel: α-actinin). Dystrophin restoration was quantified by ImageJ software and expressed as the percentage of dystrophin expression in wt muscle.

Figure 3:
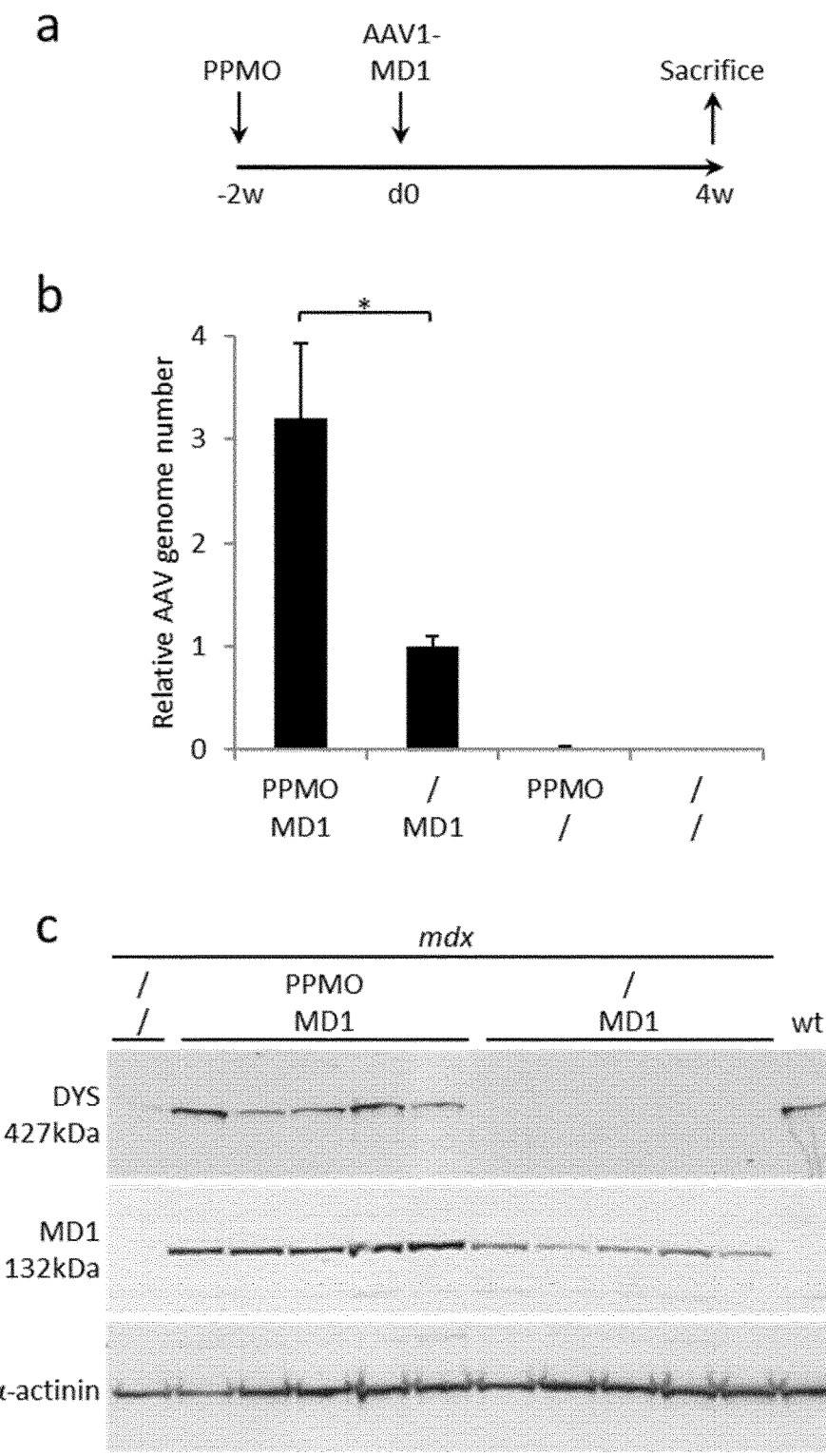

FIG. 3. Effect of Pip6a-PMO pre-treatment on AAV1 mediated micro-dystrophin gene therapy (a) Mdx TAs were injected with 1 nmole of Pip6a-PMO two weeks (−2 w) before injection of 1E+10 vg of AAV1-MD1 micro-dystrophin expressing vector (day 0, d0). Control mdx TAs were injected with PPMO or AAV1-MD1 vector alone. Five TAs were injected per group. The mice were sacrificed 4 weeks later (4 w). (b) Quantification of AAV genomes by absolute Taqman qPCR. AAV genome content is expressed as the AAV genome number relative to the value obtained for the non PPMO-treated mdx muscles. The data represent the mean values of the 5 muscles per group ±SEM. *$p<0.05$, Student's t-test. (c) Expression of PPMO-induced dystrophin (DYS, 427 kDa) and micro-dystrophin (μDYS, 132 kDa) evaluated by western blotting with MANEX1011B monoclonal antibodies (upper panel) on whole protein extracts from the treated muscles (lower panel: α-actinin).

EXAMPLES

Materials and Methods

Viral Vector Production and Animal Experiments

A three-plasmid transfection protocol was used with pAAV(U7smOPT-SD23/BP22), pAAV(U7smOPT-scr) and codon optimized pΔR4-R23/ΔCT (MD1) plasmids for generation of single-strand AAV1-U7ex23 (7), AAV1-U7scr (13) and AAV1-MD1 (37) vectors. Vector titers were determined by real-time PCR and expressed as vector genomes per ml (vg/ml). Three-month-old mdx mice were injected into the Tibialis anterior (TA) muscles with 1 nmole of Pip6a-PMO oligonucleotides (GGCCAAACCTCGGCT-TACCTGAAAT—SEQ ID NO:1) (20). Additionally, 50 μl of AAV1-U7scr, AAV1-U7ex23 or AAV1-MD1 containing 1E+10 or 1E+11 vg were injected into C57BL/6 (wt) or mdx TAs. These animal experiments were performed at the Myology Research Center, Paris, France, according to the guidelines and protocols approved by the Institutional Review Board. A minimum of four mice were injected per group for each experiments. At sacrifice, muscles were collected, snap-frozen in liquid nitrogen-cooled isopentane and stored at −80° C.

Viral Genome Quantification

Genomic DNA was extracted from mouse muscles using Puregene Blood kit (Qiagen). Copy number of AAV genomes and genomic DNA were measured on 100 ng of genomic DNA by absolute quantitative real-time PCR on a StepOnePlus™ (Applied Biosystems) using the TaqmanR Universal Master Mix (Applied Biosystems). Primers (forward: CTCCATCACTAGGGGTTCCTTG (SEQ ID NO:3) and reverse: GTAGATAAGTAGCATGGC (SEQ ID NO:4)) and probe (TAGTTAATGATTAACCC (SEQ ID NO:5)) were used to specifically amplify the viral genome sequence. As a reference sample, a pAAV plasmid was 10-fold serially diluted (from $10^7$ to $10^1$ copies). All genomic DNA samples were analyzed in duplicates.

RT-PCR Analysis

Total RNA was isolated from mouse muscle with Nucleo-Spin® RNA II (Macherey-Nagel), and reverse transcription (RT) performed on 200 ng of RNA by using the Super-script™ II and random primers (Life technologies). Non-skipped and skipped dystrophin transcripts were detected by nested PCR and quantified as described (9).

Western Blot Analysis

Protein extracts were obtained from pooled muscle sections treated with 125 mM sucrose, 5 mM Tris-HCl pH 6.4, 6% of XT Tricine Running Buffer (Bio-Rad), 10% SDS, 10% Glycerol, 5% β-mercaptoethanol. The samples were purified with the Pierce Compat-Able™ Protein Assay preparation Reagent Set (Thermo Scientific) and the total protein concentration was determined with the Pierce BCA Protein Assay Kit (Thermo Scientific). Samples were denatured at 95° C. for 5 minutes and 100 μg of protein were loaded onto Criterion XT Tris-acetate precast gel 3-8% (Bio-Rad). Membrane was probed with primary monoclonal antibodies directed against dystrophin (NCL-DYS1, 1:50, Leica Biosystems; MANEX1011B, 1:50, kindly gifted by The Muscular Dystrophy Association Monoclonal Antibody Resource (38)) and α-actinin (1:1000, Sigma-Aldrich), followed by incubation with a sheep anti-mouse secondary antibody (horseradish peroxidase conjugated; 1:15000) and Pierce ECL Western Blotting Substrate (Thermo Scientific).

Immunohistochemistry

TA sections of 12 μm were cut and examined for dystrophin expression using the NCL-DYS2 monoclonal antibody (1:50; Leica Biosystems) and a goat anti-rabbit secondary antibody Alexa 488 (1:1000; Life technologies).

Results

Effect of Dystrophin Restoration by AON Pre-Treatment on Non Therapeutic Viral Genome Maintenance In order to induce temporary dystrophin expression at the sarcolemma of mdx myofibers, mdx Tibialis anterior (TA) muscles were injected with 11 μg of Pip6a-PMO (20), a peptide-phosphorodiamidate morpholino (PPMO) antisense oligonucleotide that is particularly efficient for mdx exon skipping. The non therapeutic AAV-U7scr vectors (carrying a scrambled, non-specific sequence) were injected in the same muscles two weeks later (FIG. 1a), when dystrophin rescue was optimal, at a high dose (1E+11 viral genomes). We had previously shown that these U7scr vectors, which are unable to induce exon skipping and thereby to rescue dystrophin expression, are drastically lost within three weeks from dystrophin-deficient mdx muscle (13).

Following AON pre-treatment inducing exon skipping, three weeks after AAV1-U7scr injection, immunofluorescence staining revealed a strong dystrophin restoration and its correct localization at the sarcolemma in mdx injected muscles (FIG. 1b). Dystrophin levels were quantified in mdx muscles by western blotting and showed that the AON pre-treatment resulted in 56 to 98% of quasi-dystrophin restoration compared to normal levels (FIG. 1c). As expected (13), the viral genome content analyzed by quantitative PCR (qPCR) was 6 times higher in wild-type muscles (wt) than in non AON treated mdx muscles. Interestingly, the viral genome content analyzed by qPCR in the mdx AON treated group is similar to the one observed in wt muscles (FIG. 1d). Therefore, a significant dystrophin expression induced by PPMO pre-treatment at the time of AAV1-U7scr injection protects against the rapid loss of AAV1-U7scr genomes in mdx muscles comparable to what was observed in wt muscles.

Effect of Pip6a-PMO Pre-Treatment on Dystrophin Rescue at Low Close of Therapeutic AAV-U7ex23

AAV1 vectors encoding the U7ex23 (AAV1-U7ex23) allow efficient exon 23 skipping and therefore quasi-dystrophin rescue in the mdx muscles. To evaluate the benefit of an AON pre-treatment on the quasi-dystrophin rescue via AAV1-U7ex23, we injected 11 μg of Pip6a-PMO antisense oligonucleotides into mdx TAs two weeks before injection of AAV1-U7ex23 vectors (FIG. 2A). A low vector dose (1E+10 viral genomes) was chosen as this dose allows a weak quasi-dystrophin rescue (less than 5% of the normal levels) (13).

The benefit of AAV1-U7ex23 injection was analysed six months later when dystrophin rescue induced by the single PPMO injection was nearly abolished. Levels of exon 23 skipping analyzed by nested RT-PCR (FIG. 2b) and quantified by qPCR (FIG. 2c) in mdx TAs treated with AAV1-U7ex23 or PPMO alone were low as expected, respectively 9 and 6% of skipped transcripts, leading to the synthesis of rescued dystrophin around 2% of the normal level (FIG. 2e). Conversely, TAs treated sequentially with PPMOs and AAV1-U7ex23 showed 54% of skipped transcripts (FIG. 2c)

and 20% of the normal levels of dystrophin (FIG. 2e). AAV genome copy number quantified by absolute qPCR was 8 fold higher in the dual PPMO/AAV1-U7ex23 treated muscles than in AAV1-U7ex23 only injected muscles (FIG. 2D). These data demonstrate that the PPMO pre-treatment allowed a better maintenance of the therapeutic U7ex23 genomes in the mdx muscles six months after the AAV-U7 injections and remarkably resulted in a 10 fold improvement of the rescued dystrophin amount.

Pip6a-PMO Pre-Treatment Significantly Increases the Efficacy of AAV1 Mediated Micro-Dystrophin Gene Therapy To evaluate the efficacy of an AON pre-treatment on AAV-micro-dystrophin gene therapy, we injected Pip6a-PMO AONs into mdx TAs two weeks before injection of AAV1-MD1 vector (1E+10 vg) expressing a murine micro-dystrophin (MD1) (37) (FIG. 3a). Four weeks later, a strong dystrophin restoration was observed in PPMO-treated mdx TAs induced by the PPMO pre-treatment (FIG. 3c). AAV genome copy number and micro-dystrophin expression were 3-fold higher in the PPMO/AAV1-MD1 treated muscles than in AAV1-MD1 only treated muscles (FIG. 3b&c), illustrating the PPMO pre-treatment benefit on AAV-micro-dystrophin gene therapy. This experiment establishes the proof of concept that the AON pre-treatment is capable of enhancing all AAV-based gene therapies for DMD.

DISCUSSION

AAV genomes are rapidly lost from dystrophic muscles during AAV-U7-mediated exon-skipping therapy, certainly because of their episomal nature and the fragility of the dystrophic muscle fibers that undergo cycles of necrosis/generation, show abnormally leaky membranes, and in addition are characterized by increased excretion of exosomes and microparticles (36). We showed here that a significant (>60%) quasi-dystrophin rescue following PPMO pre-treatment at the moment of AAV-U7 injections allows an efficient maintenance of the viral genomes in mdx muscles three weeks later. Additionally, this initial maintenance of viral genomes increases quasi-dystrophin restoration by AAV-U7, around 6 fold at RNA level and around 10 fold at protein level six months later.

The PPMO pre-treatment resulted in substantial dystrophin expression at the time of AAV-U7 injection. This likely reduces, like in normal control muscle, the membrane abnormalities leading to AAV genome loss before AAV-U7 induced quasi-dystrophin expression occurs. Once established, a AAV-U7 mediated high quasi-dystrophin expression will be maintained because it will by itself prevent transgene loss. Hence, by allowing the maintenance of high viral genome content in the critical period between AAV injection and AAV-mediated transgene expression in the treated dystrophic muscles, PPMO-mediated quasi-dystrophin restoration guarantees a long-lasting benefit of AAV-U7 treatment.

This pre-treatment could be induced by any AONs allowing substantial quasi-dystrophin rescue (i.e. using different skippable mutations and different target sequences and different AON chemistries such as tricyclo-DNA (36)) using the principle demonstrated here with the PPMO chemistry.

This AON pre-treatment is applicable to all therapeutic approaches for Duchenne myopathy using AAV vectors, in particular AAV-U7-mediated exon skipping and classical gene therapy with transfer of functional micro-dystrophin cDNAs into muscles, as demonstrated thanks to the data presented herein.

On the eve of clinical trials using AAV-based therapies for DMD patients, this study underscores the strong impact of combined approaches to improve the benefit of AAV-based therapies allowing the use of lower and thus safer vector doses for a larger level of dystrophin expression in the long term.

REFERENCES

1. Harper, S. Q., Hauser, M. A., DelloRusso, C., Duan, D., Crawford, R. W., Phelp s, S. F., Harper, H. A., Robinson, A. S., Engelhardt, J. F., Brooks, S. V. et al. (2002) Modular flexibility of dystrophin: implications for gene therapy of Duchenne muscular dystrophy. Nat. Med., 8, 253-261.
2. Goemans, N. M., Tulinius, M., van den Akker, J. T., Burm, B. E., Ekhart, P. F., Heuvelmans, N., Holling, T., Janson, A. A., Platenburg, G. J., Sipkens, J. A. et al. (2011) Systemic administration of PRO051 in Duchenne's muscular dystrophy. N. Engl. J. Med., 364, 1513-1522.
3. Cirak, S., Arechavala-Gomeza, V., Guglieri, M., Feng, L., Torelli, S., Anthony, K., Abbs, S., Garralda, M. E., Bourke, J., Wells, D. J. et al. (2011) Exon skipping and dystrophin restoration in patients with Duchenne muscular dystrophy after systemic phosphorodiamidate morpholino oligomer treatment: an open-label, phase 2, dose-escalation study. Lancet, 378, 595-605.
4. Mendell, J. R., Rodino-Klapac, L. R., Sahenk, Z., Roush, K., Bird, L., Lowes, L. P., Alfano, L., Gomez, A. M., Lewis, S., Kota, J. et al. (2013) Eteplirsen for the treatment of Duchenne muscular dystrophy. Ann. Neurol., 74, 637-647.
5. Voit, T., Topaloglu, H., Straub, V., Muntoni, F., Deconinck, N., Campion, G., de Kimpe, S. J., Eagle, M., Guglieri, M., Hood, S. et al. (2014) Safety and efficacy of drisapersen for the treatment of Duchenne muscular dystrophy (DEMAND II): an exploratory, randomised, placebo-controlled phase 2 study. Lancet Neurol., 13, 987-996.
6. Brun, C., Suter, D., Pauli, C., Dunant, P., Lochmuller, H., Burgunder, J. M., Schumperli, D. and Weis, J. (2003) U7 snRNAs induce correction of mutated dystrophin pre-mRNA by exon skipping. Cell Mol. Life Sci., 60, 557-566.
7. Goyenvalle, A., Vulin, A., Fougerousse, F., Leturcq, F., Kaplan, J. C., Garcia, L. and Danos, O. (2004) Rescue of dystrophic muscle through U7 snRNA-mediated exon skipping. Science, 306, 1796-1799.
8. Denti, M. A., Rosa, A., D'Antona, G., Sthandier, O., De Angelis, F. G., Nicoletti, C., Allocca, M., Pansarasa, O., Parente, V., Musaro, A. et al. (2006) Chimeric adeno-associated virus/antisense U1 small nuclear RNA effectively rescues dystrophin synthesis and muscle function by local treatment of mdx mice. Hum. Gene Ther., 17, 565-574.
9. Goyenvalle, A., Babbs, A., Wright, J., Wilkins, V., Powell, D., Garcia, L. and Davies, K. E. (2012) Rescue of severely affected dystrophin/utrophin-deficient mice through scAAV-U7snRNA-mediated exon skipping. Hum. Mol. Genet., 21, 2559-2571.
10. Bish, L. T., Sleeper, M. M., Forb s, S. C., Wang, B., Reynolds, C., Singletary, G. E., Trafny, D., Morine, K. J., Sanmiguel, J., Cecchini, S. et al. (2012) Long-term restoration of cardiac dystrophin expression in golden retriever muscular dystrophy following rAAV6-mediated exon skipping. Mol. Ther., 20, 580-589.

11. Vulin, A., Barthelemy, I., Goyenvalle, A., Thibaud, J. L., Beley, C., Griffith, G., Benchaouir, R., Le, H. M., Unterfinger, Y., Lorain, S. et al. (2012) Muscle function recovery in golden retriever muscular dystrophy after AAV1-U7 exon skipping. Mol. Ther., 20, 2120-2133.
12. Lorain, S., Gross, D. A., Goyenvalle, A., Danos, O., Davoust, J. and Garcia, L. (2008) Transient immunomodulation allows repeated injections of AAV1 and correction of muscular dystrophy in multiple muscles. Mol. Ther., 16, 541-547.
13. Le Hir, M., Goyenvalle, A., Peccate, C., Precigout, G., Davies, K. E., Voit, T., Garcia, L. and Lorain, S. (2013) AAV Genome Loss From Dystrophic Mouse Muscles During AAV-U7 snRNA-mediated Exon-skipping Therapy. Mol. Ther., 21, 1551-1558.
14. Cartegni, L., Chew, S. L., and Krainer, A. R. (2002). Listening to silence and understanding nonsense: exonic mutations that affect splicing. Nat Rev Genet 3, 285-298.
15. Reed, R., and Maniatis, T. (1988). The role of the mammalian branchpoint sequence in pre-mRNA splicing. Genes & development 2, 1268-1276.
16. Aartsma-Rus, A., van Vliet, L., Hirschi, M., Janson, A. A., Heemskerk, H., de Winter, C. L., de Kimpe, S., van Deutekom, J. C., t Hoen, P. A., and van Ommen, G. J. (2009). Guidelines for antisense oligonucleotide design and insight into splice-modulating mechanisms. Mol Ther 17, 548-553.
17. Brown S C, Fassati A, Popplewell L, Page A M, Henry M D, Campbell K P, Dickson G. Dystrophic phenotype induced in vitro by antibody blockade of muscle alpha-dystroglycan-laminin interaction. J Cell Sci. 1999 January; 112 (Pt 2):209-16.
18. Kumar, P., Wu, H., McBride, J. L., Jung, K. E., Kim, M. H., Davidson, B. L., Lee, S. K., Shankar, P., and Manjunath, N. (2007). Transvascular delivery of small interfering RNA to the central nervous system. Nature 448, 39-43.
19. Betts, C., Saleh, A. F., Arzumanov, A. A., Hammond, S. M., Godfrey, C., Coursindel, T., Gait, M. J., and Wood, M. J. (2012). Pip6-PMO, A New Generation of Peptide-oligonucleotide Conjugates With Improved Cardiac Exon Skipping Activity for DMD Treatment. Molecular therapy Nucleic acids 1, e38.
20. Lehto, T., Castillo, A. A., Gauck, S., Gait, M. J., Coursindel, T., Wood, M. J., Lebleu, B. and Boisguerin, P. (2014) Cellular trafficking determines the exon skipping activity of Pip6a-PMO in mdx skeletal and cardiac muscle cells. Nucleic Acids Res., 42, 3207-3217.
21. Yamada, T., Das Gupta, T. K., and Beattie, C. W. (2013). p28, an anionic cell-penetrating peptide, increases the activity of wild type and mutated p53 without altering its conformation. Molecular pharmaceutics 10, 3375-3383.
22. Malhotra, M., Tomaro-Duchesneau, C., Saha, S., Kahouli, I., and Prakash, S. (2013). Development and characterization of chitosan-PEG-TAT nanoparticles for the intracellular delivery of siRNA. International journal of nanomedicine 8, 2041-2052.
23. Lundberg, M., Wikstrom, S., and Johansson, M. (2003). Cell surface adherence and endocytosis of protein transduction domains. Mol Ther 8, 143-150.
24. Lu, Q. L., Mann, C. J., Lou, F., Bou-Gharios, G., Morris, G. E., Xue, S. A., Fletcher, S., Partridge, T. A. and Wilton, S. D. (2003) Functional amounts of dystrophin produced by skipping the mutated exon in the mdx dystrophic mouse. Nat. Med., 9, 1009-1014.
25. Gregorevic P, Allen J M, Minami E, Blankinship M J, Haraguchi M, Meuse L, Finn E, Adams M E, Froehner S C, Murry C E, Chamberlain J S. rAAV6-microdystrophin preserves muscle function and extends lifespan in severely dystrophic mice. Nat Med. 2006 July; 12(7):787-9.
26. Koo T, Okada T, Athanasopoulos T, Foster H, Takeda S, Dickson G. Long-term functional adeno-associated virus-microdystrophin expression in the dystrophic CXMDj dog. J Gene Med. 2011 September; 13(9):497-506.
27. Shin J H, Pan X, Hakim C H, Yang H T, Yue Y, Zhang K, Terjung R L, Duan D. Microdystrophin ameliorates muscular dystrophy in the canine model of duchenne muscular dystrophy. Mol Ther. 2013 April; 21(4):750-7
28. Mendell J R, Campbell K, Rodino-Klapac L, Sahenk Z, Shilling C, Lewis S, Bowles D, Gray S, Li C, Galloway G, Malik V, Coley B, Clark K R, Li J, Xiao X, Samulski J, McPhee S W, Samulski R J, Walker C M. Dystrophin immunity in Duchenne's muscular dystrophy. N Engl J Med. 2010 Oct. 7; 363(15):1429-37.
29. Gao, G., Vandenberghe, L. H., Alvira, M. R., Lu, Y., Calcedo, R., Zhou, X., and Wilson, J. M. (2004). Clades of Adeno-associated viruses are widely disseminated in human tissues. J Virol 78, 6381-6388.
30. Gao, G. P., Alvira, M. R., Wang, L., Calcedo, R., Johnston, J., and Wilson, J. M. (2002). Novel adeno-associated viruses from rhesus monkeys as vectors for human gene therapy. Proc Natl Acad Sci USA 99, 11854-11859.
31. McCarty, D. M., Monahan, P. E., and Samulski, R. J. (2001). Self-complementary recombinant adeno-associated virus (scAAV) vectors promote efficient transduction independently of DNA synthesis. Gene Ther 8, 1248-1254.
32. Cazzella, V., Martone, J., Pinnaro, C., Santini, T., Twayana, S. S., Sthandier, O., D'Amico, A., Ricotti, V., Bertini, E., Muntoni, F., et al. (2012). Exon 45 skipping through U1-snRNA antisense molecules recovers the Dys-nNOS pathway and muscle differentiation in human DMD myoblasts. Mol Ther 20, 2134-2142.
33. De Angelis, F. G., Sthandier, O., Berarducci, B., Toso, S., Galluzzi, G., Ricci, E., Cossu, G., and Bozzoni, I. (2002). Chimeric snRNA molecules carrying antisense sequences against the splice junctions of exon 51 of the dystrophin pre-mRNA induce exon skipping and restoration of a dystrophin synthesis in Delta 48-50 DMD cells. Proc Natl Acad Sci USA 99, 9456-9461.
34. Goyenvalle, A., Vulin, A., Fougerousse, F., Leturcq, F., Kaplan, J. C., Garcia, L., and Danos, 0. (2004). Rescue of dystrophic muscle through U7 snRNA-mediated exon skipping. Science 306, 1796-1799.
35. Schumperli, D., and Pillai, R. S. (2004). The special Sm core structure of the U7 snRNP: far-reaching significance of a small nuclear ribonucleoprotein. Cell Mol Life Sci 61, 2560-2570.
36. Duguez, S., Duddy, W., Johnston, H., Laine, J., Le Bihan, M. C., Brown, K. J., Bigot, A., Hathout, Y., Butler-Browne, G. and Partridge, T. (2013) Dystrophin deficiency leads to disturbance of LAMP1-vesicle-associated protein secretion. Cell Mol. Life Sci., 70, 2159-2174.
37. Foster, H., Sharp, P. S., Athanasopoulos, T., Trollet, C., Graham, I. R., Foster, K., Wells, D. J., Dickson, G. (2008) Codon and mRNA sequence optimization of microdystrophin transgenes improves expression and physiological outcome in dystrophic mdx mice following AAV2/8 gene transfer. Mol. Ther., 16, 1825-1832.
38. Bartlett, R. J., Stockinger, S., Denis, M. M., Bartlett, W. T., Inverardi, L., Le, T. T., thi Man, N., Morris, G. E., Bogan, D. J., Metcalf-Bogan, J., Kornegay, J. N. (2000) In vivo targeted repair of a point mutation in the canine dystrophin gene by a chimeric RNA/DNA oligonucleotide. Nat. Biotechnol., 18, 615-622.

The invention claimed is:

1. A combination therapy method comprising:
   administering to a human subject an isolated antisense oligonucleotide (AON) between 10 and 40 nucleotides in length capable of inducing an exon-skipping in a dystrophin pre-mRNA thereby inducing functional dystrophin expression, and
   subsequently administering to the subject at least one viral vector encoding a Duchenne muscular dystrophy therapeutic product selected from (i) an antisense oligonucleotide able to induce exon-skipping within a dystrophin pre-mRNA, (ii) a dystrophin gene-editing endonuclease, and (iii) a functional dystrophin protein;
   wherein the pretreatment with the AON prevents the loss of therapeutic viral vector genomes from the muscles of the subject.

2. The method of claim 1, wherein said AON is administered as a pretreatment 1-40 days before administration of the viral vector.

3. The method of claim 1, wherein the viral vector is an AAV vector.

4. The method of claim 1, wherein said AON is a phosphorodiamidate morpholino oligomer.

5. The method of claim 1, wherein said AON is a peptide-phosphorodiamidate morpholino oligomer.

6. The method of claim 1, wherein said AON is a Pip6a-PMO oligomer.

7. The method of claim 1, wherein said viral vector encodes an U7-AON.

8. The method of claim 1, wherein said viral vector encodes a functional truncated dystrophin.

9. The method of claim 1, wherein said AON is administered as a pretreatment 12-16 days before administration of the viral vector.

10. The method of claim 1, wherein said AON is administered as a pretreatment 14-28 days before administration of the viral vector.

11. The method of claim 1, wherein said AON is administered as a pretreatment at least one week before administration of the viral vector.

12. The method of claim 1, wherein said AON is administered as a pretreatment at least two weeks before administration of the viral vector.

13. The method of claim 1, wherein said AON is between 15 and 40, or 20 and 40, or 25 and 40 nucleotides in length.

* * * * *